(12) United States Patent
Wezurek et al.

(10) Patent No.: US 6,202,472 B1
(45) Date of Patent: Mar. 20, 2001

(54) GAS SENSOR WITH FLASHBACK BARRIER

(75) Inventors: Horst Wezurek, Ratzeburg; Hans-Jürgen Bahs, Offendorf, both of (DE)

(73) Assignee: Dräger Sicherheitstechnik GmbH (DE)

( * ) Notice: Subject to any disclaimer, the term of this patent is extended or adjusted under 35 U.S.C. 154(b) by 0 days.

(21) Appl. No.: 09/220,318

(22) Filed: Dec. 23, 1998

(30) Foreign Application Priority Data

Jul. 10, 1998 (DE) .............................................. 198 30 870

(51) Int. Cl.[7] .......................... G01N 27/12; G01N 37/00
(52) U.S. Cl. ...................... 73/31.05; 73/23.31; 73/25.05; 73/31.02
(58) Field of Search ............................... 73/23.31, 25.05, 73/30.04, 31.01, 31.02, 31.03, 31.05

(56) References Cited

U.S. PATENT DOCUMENTS

| 3,476,517 | 11/1969 | Smith . | |
|---|---|---|---|
| 3,950,980 | * 4/1976 | Braun et al. | 73/31.05 |
| 3,985,017 | * 10/1976 | Goldsmith | 3/31.02 |

FOREIGN PATENT DOCUMENTS

| 15 98 578 | 8/1977 | (DE) | 73/31.05 |
|---|---|---|---|
| 26 24 562 A1 | 12/1977 | (DE) . | |
| 40 41 470 A1 | 6/1992 | (DE) . | |
| 0 764 847 | 3/1997 | (EP) | 73/31.05 |
| 6-66753 | * 3/1994 | (JP) | 73/31.05 |
| 6-300726 | * 10/1994 | (JP) | 73/31.05 |
| 07260686 | 10/1995 | (JP) | 73/31.05 |
| 15806 | * 7/1994 | (WO) | 73/31.05 |

* cited by examiner

*Primary Examiner*—Daniel S. Larkin
(74) *Attorney, Agent, or Firm*—McGlew and Tuttle, P.C.

(57) ABSTRACT

An explosion-proof gas sensor (1) with a flashback barrier (2) permeable to the gas to be measured between the measuring space (4) and the environment in an otherwise gas-impermeable housing (3) is described. The sensor provides reduced response time and higher signal sensitivity for the gas to be measured. A flashback barrier (2) is provided including a plurality of flexurally rigid fabric layers made preferably of metal, which are permeable to the gas to be measured, with an overall thickness of one to ten mm, an overall porosity of at least twenty percent by volume relative to the volume of the flashback barrier (2), and with a maximum number of one percent of all pores with a pore size larger than 240 $\mu$m.

20 Claims, 3 Drawing Sheets

GAS SENSOR WITH FLASHBACK BARRIER

FIELD OF THE INVENTION

The present invention pertains to a gas sensor with a flashback barrier permeable to the gas to be measured between the measuring space and the environment in the otherwise gas-impermeable housing of the gas sensor.

BACKGROUND OF THE INVENTION

Gas sensors are based on different principles of action, which are used predominantly depending on the intended use. An exemplary, special application of certain gas sensors is the measurement of the concentration of inflammable or explosive gases in mixtures with air, e.g., of methane in air. A gas concentration to be detected is measured here in a measuring chamber, into which the air-gas mixture to be measured flows due to diffusion or into which it is delivered by means of a pump, by means of the gas sensor measuring elements proper, i.e., with elements to which electric current is applied, such as pellistors, optoelectronic, or semiconductor elements. In the case of the pellistors, one of the two measuring elements is catalytically prepared, while the second measuring element does not have this catalytic preparation. The behavior of the change in the resistance of the catalytically prepared measuring element compared with the second one, which behavior is characteristic of the gas to be detected, can be evaluated by means of prior-art resistance-measuring bridges.

A gas sensor for combustible gases with electrically heatable measuring elements and corresponding resistance-measuring bridges has become known from DE 15 98 578 C3, wherein, e.g., a very fine-mesh screen or a plate provided with very narrow perforations is provided as an ignition barrier in front of the measuring chamber.

Such ignition barriers or flashback barriers are of utmost significance in the gas sensors being described in order to reliably prevent the gas to be detected, which is being burned in the measuring chamber under controlled conditions, from igniting the gas present in the mixture outside the measuring chamber, i.e., for instance, methane in air.

In the case of the use of infrared optical (optoelectronic) elements, it is desirable to have an effective flashback barrier between the measurement space in the gas sensor and the ambient atmosphere. Corresponding gas sensors with flashback barriers are therefore called explosion-proof

SUMMARY AND OBJECTS OF THE INVENTION

The object of the present invention is to propose a gas sensor with an improved flashback barrier, which can be obtained in a high, uniform quality from available combinations of materials.

According to the invention, a gas sensor with a flashback barrier permeable to the gas to be measured is provided between the measuring space and the environment in the otherwise gas-impermeable housing of the gas sensor. The flashback barrier includes a plurality of flexurally rigid fabric layers permeable to the gas to be measured. The layers have an overall thickness of one to ten mm with an overall porosity of at least twenty percent by volume relative to the volume of the flashback barrier. The layers have a one percent maximum number of all pores with a pore size larger than 240 $\mu$m.

The essential advantages of the present invention relate to the improved, shorter response time as well as the higher measuring sensitivity of the gas sensors equipped with the flashback barriers of the invention as compared with the otherwise identical gas sensors, which are provided with flashback barriers made of sintered metal, which have been used to date.

It was thus possible to increase the measuring sensitivity by nearly forty percent and to reduce the response time by more than half in a gas sensor according to the present invention, always compared with an identical gas sensor with a flashback barrier made of sintered metal.

Retrospectively, the improved action of the present invention can probably be explained by the fact that sintered metal barriers for gas sensors can assume the required dual function, namely, the ventilating function, on the one hand, and a reliable flashback barrier function, on the other hand, only at the expense of safety. Relatively long response times and lower signal levels of the gas sensors can be observed with the prior-art solution for the flashback barrier made of sintered metals.

The reduced safety for the flashback barrier made of sintered metals is explained by the fact that the manufacture of sintered compacts and especially the distribution of the pore sizes, which is associated with this and is important in this connection, are subject to relatively great manufacturing tolerances. The maximum allowable pore sizes are rather limited in practice and the ventilating function is relatively suppressed as a result in favor of the flashback barrier function. The consequence is longer response times and reduced signal levels of the prior-art gas sensors.

The essential content of the technical teaching according to the present invention is the arrangement of a plurality of individual, flexurally rigid fabric layers made especially of metals for a flashback barrier for explosion-proof gas sensors, which are permeable to the gas to be measured. The suitable metals include steel, CrNi alloys, pure nickel, MONEL (i.e., an alloy of nickel, copper, iron, and manganese) copper, Al alloys, titanium, or precious metals, individually or combined.

Other suitable materials for the fabric layers are glasses, ceramic materials, or even plastics, especially heat-resistant plastics.

The individual fabric layers of a flashback barrier may consist of different materials, but metallic materials are especially preferred.

The individual fabric layers of an arrangement have, in general, different designs in order to obtain an optimal combination of properties. The thickness of a flashback barrier is one to ten mm. The overall porosity of the flashback barrier is at least twenty percent by volume, and preferably thirty to seventy percent by volume relative to the total volume of the flashback barrier. It has, on the whole, a maximum number of one percent of all pores with a pore size larger than 240 $\mu$m. The topmost fabric layer facing the outside may be selected to be relatively coarse in order to protect the subjacent fabric layer which prevents the flashback from mechanical damage, This fabric layer determines the quality of the safety against ignition flashback.

One or more relatively coarsely woven fabric layers are arranged under it, which assume a support function for the entire fabric arrangement. The latter, lowermost fabric layers are provided with relatively larger openings (pore or mesh sizes) compared with the first, topmost fabric layers. The individual fabric layers arranged one on top of another are preferably assembled by pressing or sintering, i.e., under the action of pressure and heat, or are formed in the form of a laminate. The thickness of the flashback barrier and consequently the diffusion path for the gas to be detected is preferably a few mm, especially one to five mm.

The gas sensors according to the present invention contain the gas-permeable flashback barriers for limiting the measuring space from the ambient atmosphere such that the connection to the otherwise gas-impermeable sensor housing takes place in the edge area without a gap. Electric welding is preferably employed for connection in the case of preferred metal housings, and the flashback barrier is preferably fused into the plastic housing in the case of plastic housings. Additional prior-art connection techniques well known to the person skilled in the art may conceivably be used.

The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which preferred embodiments of the invention are illustrated.

DESCRIPTION OF THE PREFERRED EMBODIMENTS

Figure 1:
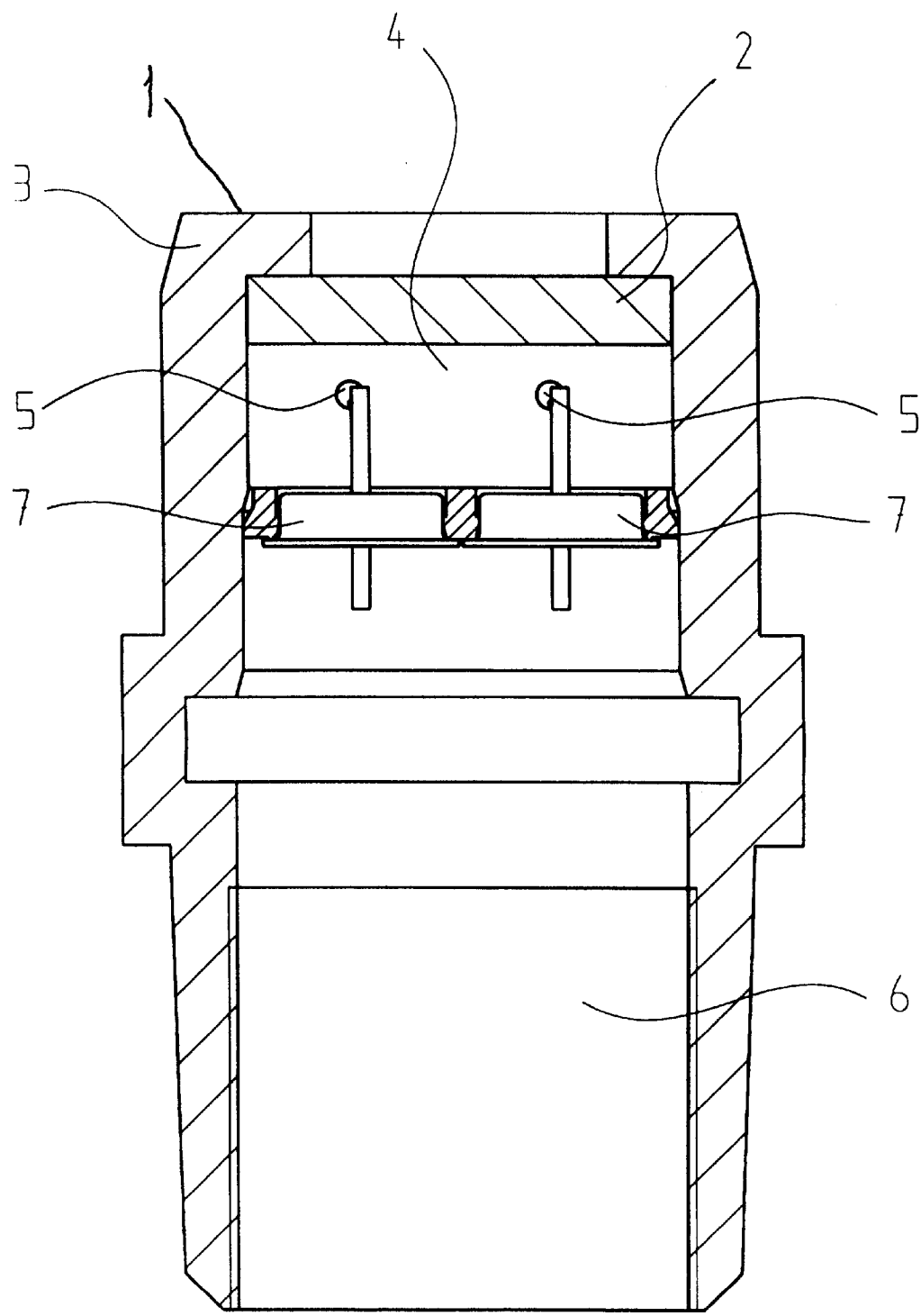
FIG. 1 is a schematic sectional view of an embodiment of a gas sensor according to the present invention.

Referring to the drawings in particular, a circularly cylindrical gas sensor 1 shown in FIG. 1 is provided with a pressure-encapsulated, gas-impermeable housing 3 made of steel in an explosion-proof manner. The gas to be measured (e.g., methane), or hydrogen, or ammonia enters (diffuses) from the environment through the crater-like opening in the housing 3 and through the flashback barrier 2 which is permeable for the gas to be measured.

Figure 3:
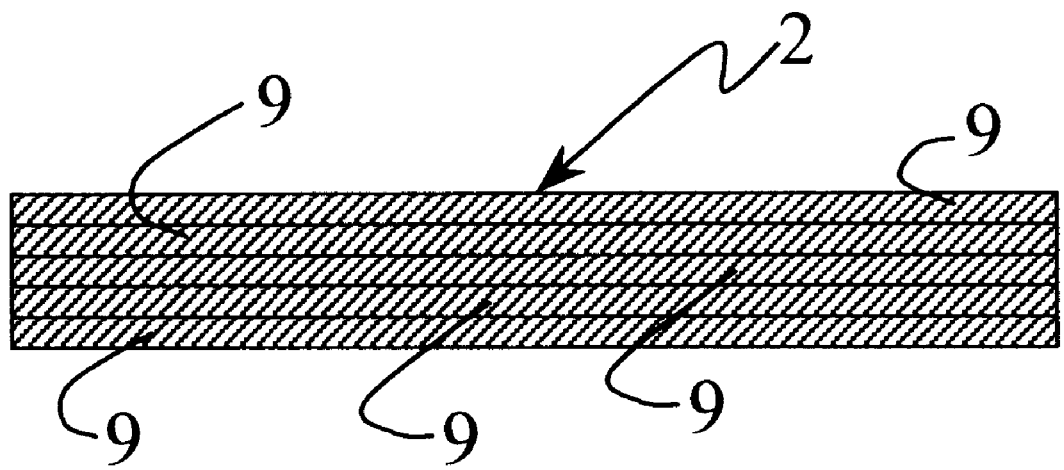
FIG. 3 is a schematic sectional view of the plurality of flexurally rigid fabric layers used to form the flashback barrier.

The permeable flashback barrier 2 is made of a plurality of flexurally rigid fabric layers 9 made of metal, as shown in FIG. 3. The fabric layers 9 or fabric structures are web-like. The flashback barrier 2 is based on a plurality of the web-like fabric structures 9 which are combined. The assembling of the fabric layers 9 may be by sintering (by heating and pressing) such that the various fabric layers 9 are connected. The flashback barrier 2 must ensure that no igniting spark can enter the environment from the measuring space 4 in order to reliably prevent an explosion of the gas mixture in the ambient air. The measuring elements 5 are either pellistors, semiconductor elements, heat conduction elements, optoelectronic, or other gas-sensitive electronic components.

In the case of pellistors, one of the two measuring elements 5 is, in particular, prepared on the outside with a catalyst characteristic of the gas to be detected in order to trigger a controlled combustion in the presence of the gas to be detected. This, combustion leads to a change in resistance due to the increased temperature compared with the second measuring element 5. This change in resistance can be detected preferably in a resistance measuring bridge circuit, not shown, and this change ultimately indicates the concentration of the gas to be measured (measured gas).

The disk-shaped flashback barrier 2 of the embodiment of FIG. 1 is preferably welded in a ring-shaped pattern in the housing 3; and thus it becomes its integral part. The consequence of the use of the flashback barrier welded, as noted, is that no gap lengths of at least, e.g., five mm are specified and to be complied with for approval, unlike in the case of the use of sintered metal disks with a correspondingly required thickness. That is, by using the barrier 2 and making it an integral part of the housing 3 by welding, obtaining approval by governmental or technical entities will not require the provision or guarantee of gap lengths of a certain dimension. For example, five mm has been required for conventional prior art sintered metal disks to prevent explosions. The inventive barriers of the invention need not exceed this thickness. The flashback barrier 2 according to the present invention has a markedly smaller overall thickness of especially about one to five mm, with preferably two to five fabric layers 9 made of steel. There is a correspondingly short diffusion path for the gas to be detected, shorter response times for the measurement, and better measuring sensitivity.

The pore size of the individual fabric layers 9 is advantageously twenty to eighty $\mu$m. To ensure the functional reliability of the gas sensors 1 according to the present invention, it is always necessary, according to empirical results, that at most one percent of all pores have a pore size larger than 240 $\mu$m or that at least ninety-nine percent of all pores (openings) of the flashback barrier 2 have a pore size smaller than 240 $\mu$m. The cable bushings of the cables leading to the measuring elements 5 are cast in a gas-tightly sealed plastic block 6. The measuring elements 5 are held in a defined position by means of two brackets 7 made of a suitable plastic or ceramic. Measurements have shown that in the case of methane, the response time (so-called t 90 time) decreases from about twenty seconds to about ten seconds and the measuring sensitivity for methane increases from 1.5 to 2.0 units in the case of gas sensors 1 according to the present invention with flashback barriers 2 compared with otherwise identical gas sensors 1 with disk-shaped flashback barriers made of sintered metal.

Figure 2:
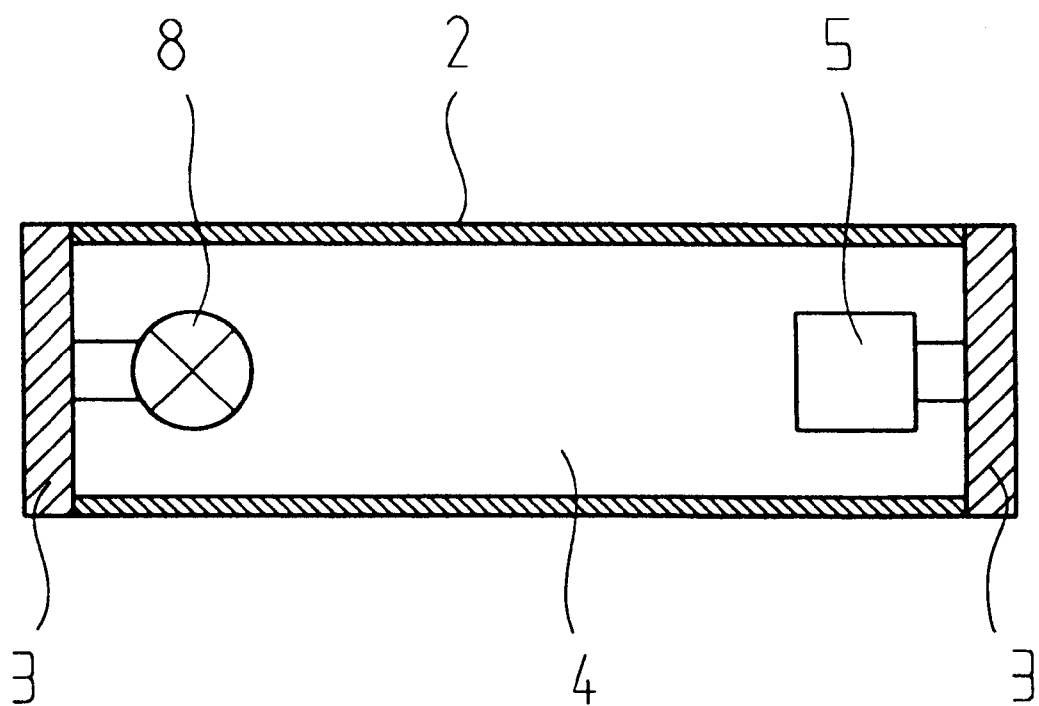
FIG. 2 is a schematic sectional view of another embodiment of a gas sensor according to the present invention.

FIG. 2 shows as an alternative an infrared optical measuring set-up with a radiation source 8 and with the infrared optical measuring element 5. The radiation source 8 and the infrared optical measuring element 5 define the absorption-measuring path in the measuring space 4. The flashback barrier 2 according to the present invention forms the limitation of the measuring space 4 from the ambient atmosphere here as well.

The flashback barrier 2 is also connected to the housing 3 in the edge area without a gap, especially by welding or fusion, in this embodiment as well.

While specific embodiments of the invention have been shown and described in detail to illustrate the application of the principles of the invention, it will be understood that the invention may be embodied otherwise without departing from such principles.

What is claimed is:

1. A gas sensor arrangement comprising:
   a gas-impermeable housing defining a measuring space; and
   a flashback barrier permeable to the gas to be measured disposed between the measuring space and the environment to provide a gas permeable area in the otherwise gas-impermeable housing, said flashback barrier including a plurality of flexurally rigid fabric layers permeable to the gas to be measured, said barrier having an overall thickness of one to ten mm with an overall porosity of at least twenty percent by volume relative to the volume of said flashback barrier and with a maximum percentage of pores with a pore size larger than 240 μm equal to one percent.

2. The gas sensor arrangement in accordance with claim 1, wherein said flashback barrier comprises two to five fabric layers and has an overall thickness of one to five mm.

3. The gas sensor arrangement in accordance with claim 1, wherein said fabric layers consist of one or more of a ceramic material, glass, a plastic, or a metal.

4. The gas sensor arrangement in accordance with claim 3, wherein said metal is one or more of a steel, a chromium-nickel alloy, nickel, a nickel-copper-iron-manganese alloy, copper, an aluminum alloy, titanium, or a precious metal.

5. The gas sensor arrangement in accordance with claim 1, wherein said flashback barrier is welded or fused to said housing.

6. The gas sensor arrangement in accordance with claim 1, wherein said fabric layers are one of sintered or pressed together or are connected in the form of a laminate.

7. A process of measuring the concentration of hydrocarbons, the process comprising, the steps of:

providing a gas-impermeable housing defining a measuring space;

providing a flashback barrier permeable to the gas to be measured disposed between the measuring space and the environment to provide a gas permeable area in the otherwise gas-impermeable housing, said flashback barrier including a plurality of flexurally rigid fabric layers permeable to the gas to be measured, said barrier having an overall thickness of one to ten mm with an overall porosity of at least twenty percent by volume relative to the volume of said flashback barrier and with a maximum percentage of pores with a pore size larger than 240 μm equal to one percent;

providing a measuring element in the measuring space; and measuring the concentration of hydrocarbons that enters the measuring space from the environment.

8. The process in accordance with claim 7, wherein said flashback barrier comprises two to five fabric layers and has an overall thickness of one to five mm.

9. The process in accordance with claim 7, wherein said fabric layers consist of one or more of a ceramic material, glass, a plastic, or a metal.

10. The process in accordance with claim 9, wherein said metal is one or more of a steel, a chromium-nickel alloy, nickel, a nickel-copper-iron-manganese alloy, copper, an aluminum alloy, titanium, or a precious metal.

11. The process in accordance with claim 7, wherein said flashback barrier is welded or fused to said housing.

12. The process in accordance with claim 7, wherein said fabric layers are one of sintered or pressed together or are connected in the form of a laminate.

13. The process in accordance with claim 7, wherein said step of measuring the concentration of hydrocarbons that enters the measuring space from the environment includes one of measuring for methane, hydrogen, or ammonia.

14. A gas sensor comprising:

a gas-impermeable housing defining a measuring space;

a measuring element disposed in said measuring space; and a flashback barrier permeable to the gas to be measured disposed between the measuring space and the environment to provide a gas permeable area in the otherwise gas-impermeable housing, said flashback barrier including a plurality of flexurally rigid fabric layers permeable to the gas to be measured, said barrier having an overall thickness of one to ten mm with an overall porosity of at least twenty percent by volume relative to the volume of said flashback barrier and with a maximum percentage of pores with a pore size larger than 240 μm equal to one percent.

15. The gas sensor in accordance with claim 14, wherein said flashback barrier comprises two to five fabric layers and has an overall thickness of one to five mm.

16. The gas sensor in accordance with claim 14, wherein said fabric layers consist of one or more of a ceramic material, glass, a plastic, or a metal.

17. The gas sensor in accordance with claim 14, wherein said metal is one or more of a steel, a chromium-nickel alloy, nickel, a nickel-copper-iron-manganese alloy, copper, an aluminum alloy, titanium, or a precious metal.

18. The gas sensor in accordance with claim 16, wherein said flashback barrier is welded or fused to said housing.

19. The gas sensor in accordance with claim 16, wherein said fabric layers are one of sintered or pressed together or are connected in the form of a laminate.

20. The gas sensor in accordance with claim 16, wherein said measuring element measures the concentration of hydrocarbons that enters the measuring space from the environment.

* * * * *